United States Patent [19]

Holtkamp

[11] Plant 4,773

[45] Oct. 6, 1981

[54] AFRICAN VIOLET PLANT

[76] Inventor: Reinhold Holtkamp, Werther Strasse 112, D-4294 Isselburg, Fed. Rep. of Germany

[21] Appl. No.: 172,219

[22] Filed: Jul. 25, 1980

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet named Massachusetts, particularly characterized by its profuse flowering, with up to 15 stems carrying up to 12 or more individual flowers; lilac flower color, with a deeper purple color near the center; long lasting, non-dropping flowers, and by its compact, vigorous growth habit.

1 Drawing Figure

The present invention comprises a new and distinct cultivar of African violet plant, botanically known as *Saintpaulia ionantha,* and hereinafter referred to by the cultivar name Massachusetts.

The new cultivar was referred to during the breeding and selection process by the designation D210/20 and 480, and is a product of a planned breeding program. The basic objective of the breeding program was to create a new African violet cultivar having a rich flower bouquet or corolla, with lilac flower color.

The new cultivar was originated from a cross made in a controlled breeding program in Isselburg, West Germany. The female, or seed parent was Wisconsin, disclosed in my U.S. Plant Pat. No. 4,353. The male, or pollen parent, was a cultivar designated b. 229/11, an unpatented, pink star, semi-double variety.

The new cultivar Massachusetts was discovered and selected by me as a flowering plant within the progeny of the stated cross in a controlled environment in Isselburg, West Germany. Asexual reproduction of the new cultivar by vegetative cuttings, as performed by me at Isselburg, West Germany, has demonstrated that the combination of characteristics as herein disclosed for the new cultivar are firmly fixed and are retained through successive generations of asexual reproduction.

Massachusetts has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Massachusetts, which in combination distinguish this African violet as a new and distinct cultivar:

1. Generally lilac flower color, with a more deep purple center.
2. Profuse flowering, with up to 15 flower stems carrying up to 12 and more individual flowers.
3. Long lasting, non-dropping flowers.
4. Compact, vigorous growth habit.
5. In the second flowering, Massachusetts tends to produce more semi-double blossoms.

The new cultivar is most similar to the maternal parent Wisconsin. Massachusetts is principally distinguished from Wisconsin by its lilac flower color, with deeper purple centers, and its more profuse flowering.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Massachusetts.

Parentage:

*Male parent.*—b. 229/11, a pink star, semi-double variety.

*Female parent.*—Wisconsin (U.S. Plant Pat. No. 4,353).

Propagation: The new cultivar holds its distinguishing characteristics through successive propagations by leaf cuttings.

Plant: From 8 cm. to 10 cm. tall when grown in pots, and approximately 25–30 cm. in diameter when fully grown.

Leaves:

*General form.*—Round to oval.

*Diameter.*—Up to 55–65 mm.

*Texture.*—Soft and hairy.

*Aspect.*—Velvety, slightly shiny.

*Veins.*—Upperside slightly visible; underside well-pronounced and shiny; on younger leaves underside light brownish-purple, older leaves glassy and light green.

*Color (upperside).*—HCC Spinach Green 0960.

*Color (underside).*—HCC Willow Green 000862/2.

*Petiole.*—Old plants, light green-purple, hairy; younger plants, brown-purplish, very hairy.

Flowers:

*Buds.*—Ball shaped, 6–8 mm. just before opening; 8–12 per stem.

*Sepals.*—Color: greenish-brown, hairy. Calyx: flat, funnel-shaped. Aspect: spear-shaped. Peduncle: strong, upright.

Individual flowers:

*Size.*—Between 35–45 mm. in total diameter.

*Color.*—Upperside: Bishop's Violet 34/1; center Royal Purple 834. Underside: Bishop's Violet 34/2.

*Borne.*—Flowers are carried on strong upright peduncles. Some blossoms display an additional small petal in the center of the flower.

*Shape.*—Conventional violet shape; 2 large, 3 small petals; on second and subsequent flowering, more semi-doubling appears.

*Corolla.*—Profuse.

*Flowering time.*—6–7 weeks after potting first flowers appear; 8–10 weeks to flowering, saleable plant.

Reproductive organs:

*Anthers.*—2, composed of 4 cells with seed capsule pushed slightly through; color sulphur yellow/1.

*Filaments.*—3–4 mm. long; base, purple changing into light green.

*Styles.*—7 mm. Violet Purple 733.

*Pollen color.*—HCC Dresden Yellow 64/2.

Roots: White when young and active; older roots velvety; normally developed.

Disease resistance: Good as experienced to date.

General observations: Massachusetts is a profuse flowering variety which has long-lasting, non-dropping lilac flowers with dark purple centers.

I claim:

1. A new and distinct cultivar of African violet known by the cultivar name Massachusetts, as described and illustrated, and particularly characterized by its profuse flowering, with up to 15 stems carrying up to 12 or more individual flowers; lilac flower color, with a deeper purple color near the center; long lasting, non-dropping flowers, and by its compact, vigorous growth habit.

* * * * *

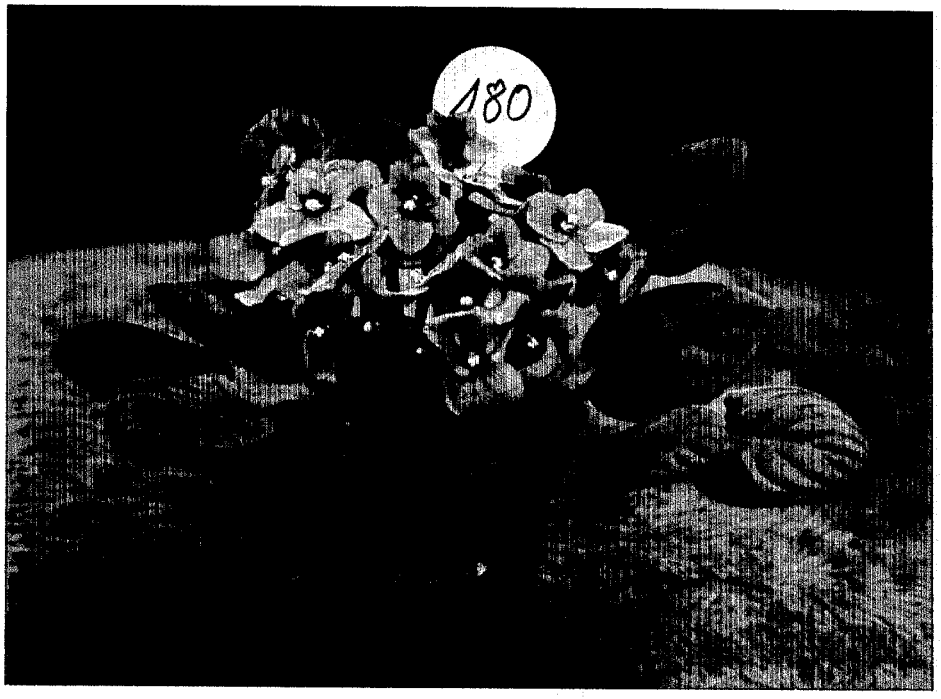
180